United States Patent [19]

Ancher et al.

[11] Patent Number: 4,517,197

[45] Date of Patent: May 14, 1985

[54] -N-SUBSTITUTED PHENYL-5-METHOXYMETHYL-2-OXAZOLIDINONES AND PHARMACEUTICAL COMPOSITIONS CONTAINING SAME

[75] Inventors: Jean-François R. Ancher, Rueil Malmaison; Guy R. Bourgery, Colombes; Philippe L. Dostert; Colette A. Douzon, both of Paris; Patrick G. Guerret, Rueil Malmaison; Alain P. Lacour, La Varenne; Michel Langlois, Buc, all of France

[73] Assignee: Delalande S.A., Courbevoie, France

[21] Appl. No.: 518,320

[22] Filed: Jul. 29, 1983

Related U.S. Application Data

[63] Continuation of Ser. No. 265,501, May 20, 1981, abandoned.

[30] Foreign Application Priority Data

Jun. 4, 1980 [FR]  France ................................ 80 12423

[51] Int. Cl.$^3$ ................. C07D 263/24; A61K 631/42
[52] U.S. Cl. .................................... 514/376; 548/229; 548/231; 548/232
[58] Field of Search ...................... 548/232, 229, 231; 424/272

[56] References Cited

U.S. PATENT DOCUMENTS

| 3,654,298 | 4/1972 | Douzon et al. ..................... 548/232 |
| 3,655,687 | 4/1972 | Fauran et al. ...................... 548/232 |
| 4,150,029 | 4/1979 | Dostert et al. ..................... 548/232 |
| 4,250,318 | 2/1981 | Dostert et al. ..................... 548/232 |

FOREIGN PATENT DOCUMENTS

| 2028306 | 3/1980 | United Kingdom ............... 548/232 |
| 2054575 | 2/1981 | United Kingdom ............... 548/232 |

Primary Examiner—Robert Gerstl
Assistant Examiner—S. A. Gibson
Attorney, Agent, or Firm—Flynn, Thiel, Boutell & Tanis

[57] ABSTRACT

A compound of the formula

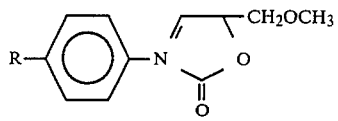

where R is selected from the group consisting of $CH_3-CO-(CH_2)_2-O-$,

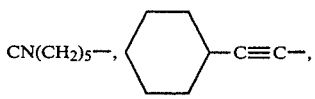

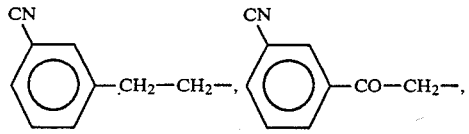

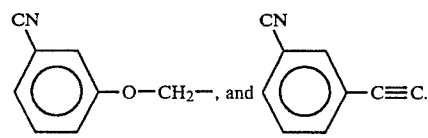

The compounds are useful in treating depression.

9 Claims, No Drawings

N-SUBSTITUTED PHENYL-5-METHOXYMETHYL-2-OXAZOLIDINONES AND PHARMACEUTICAL COMPOSITIONS CONTAINING SAME

This application is a continuation of U.S. Ser. No. 265,501, filed May 20, 1981, now abandoned.

The present application relates to N-aryl 2-oxazolidinones, the process for preparing the same and their application in therapeutics.

More precisely, these compounds correspond to the general formula:

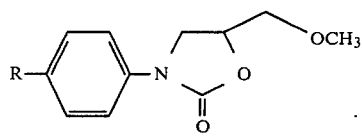
(I)

in which R designates:
- the (2-acetyl) ethyloxy chain of formula: CH$_3$CO—(CH$_2$)$_2$—O;
- the (5-cyano) n-pentyl chain of formula: CN—(CH$_2$)$_5$—;
- the p-chlorophenyl or m-cyanophenyl nucleus;
- the (2-cyclohexyl) ethynyl chain of formula:

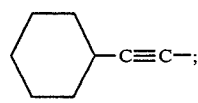

or
a group of structure:

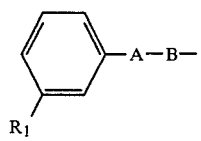

where R$_1$ represents a halogen atom or the cyano group and the —A—B— chain has any one of the following meanings: —CH$_2$—CH$_2$—, —CO—CH$_2$—, —O—CH$_2$—, —C≡C—, —CH$_2$—CH$_2$—O—.

The present invention also relates to the processes for preparing these compounds.

Thus:

A. The compound of formula (I) where R represents the CH$_3$CO—(CH$_2$)$_2$—O— chain is obtained by acid hydrolysis of the compound of formula:

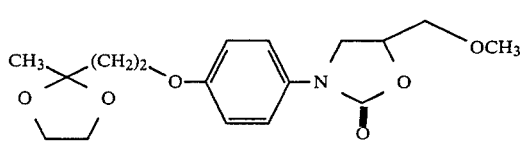
(II)

the acid conditions being obtained preferably by means of hydrochloric and sulfuric acid and the hydrolysis being carried out in an organic solvent such as THF or acetone.

The compound of formula (II) is obtained by condensation of the chlorinated, brominated, mesylated or tosylated derivative of 2-hydroxyethyl 2-methyl 1,3-dioxolane preferably in a DMF, acetone or acetonitrile medium, and in the presence of potassium carbonate or potassium hydride with the compound of formula:

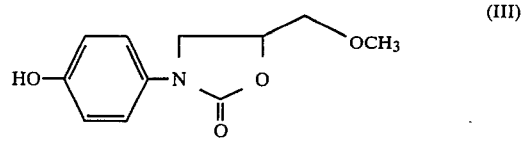
(III)

prepared in accordance with the procedure described in Belgian Pat. No. 876 831.

B. The compound of formula (I) where R represents the CN—(CH$_2$)$_5$— chain is obtained by a two-step synthesis which consists in treating the compound of formula:

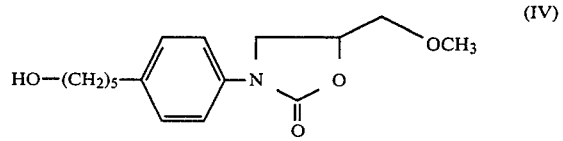
(IV)

with mesyl chloride, in an organic solvent such as methylene chloride, preferably cold and in presence of a base such as triethylamine, then in reacting, on the compound obtained, potassium or sodium cyanide in an organic solvent such as DMSO.

The compound of formula (IV) is obtained by catalytic debenzylation in an ethanol medium and in the presence of palladium on charcoal at 5%, of the compound of formula:

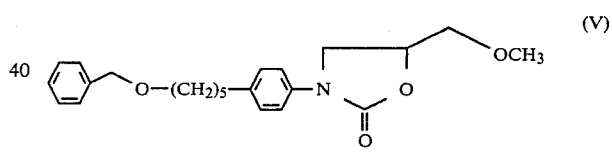
(V)

the latter being obtained by cyclisation by means of a 10% phosgene solution in dichloroethane in the presence of potassium carbonate or triethylamine, of the compound of formula:

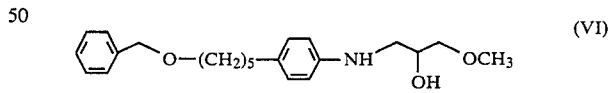
(VI)

itself obtained by condensation of 3-methoxy 1,2-epoxy propane, in an alcohol medium, with an aniline of the formula:

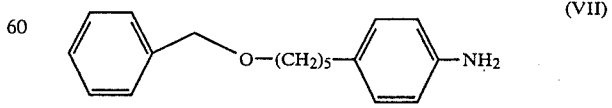
(VII)

The aniline of formula (VII) is, for its part, obtained by reduction by means of triethylsilane (HSiEt$_3$) in the presence of trifluoroacetic acid, of cetoaniline of formula:

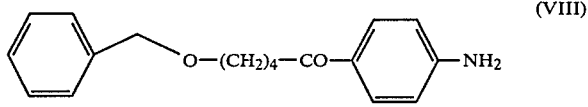

(VIII)

This latter is obtained by reduction by means of iron in the presence of 10% ammonium chloride in water and ethanol, of the nitrated derivative of formula:

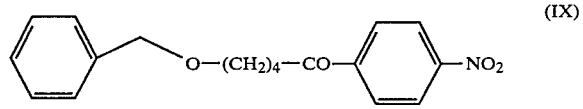

(IX)

obtained by condensation of 4-benzyloxy n-butanal in the presence of potash, in a methanol or T.H.F. medium, with the α-phenylamino p-nitrobenzylester of diphenyl phosphorous acid.

It should be noted that it is also possible to obtain the compounds of formula (V) by cyclisation by means of ethanolic potash or sodium methylate in a methanol medium, of the compound of formula:

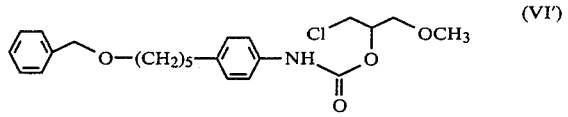

(VI')

C. The compounds of formula (I) in which R represents the p-chlorophenyl, m-cyanophenyl, m-cyanobenzoylmethyl or m-halogenobenzoylmethyl, are obtained: either by cyclisation with ethanolic potash or sodium methylate in a methanol medium, of the compound of formula:

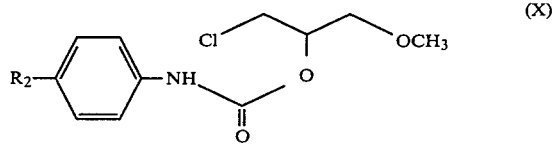

(X)

in which $R_2$ takes one of the four particular values of R given above. The compounds of formula (X) are obtained by action of phosgene on 1-chloro 3-methoxy 2-propanol, then by reaction of the intermediate compound thus prepared with an aniline of formula:

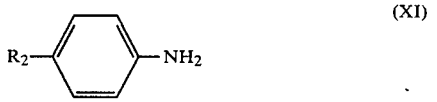

(XI)

in which $R_2$ has the same values as in formula (X).

The compounds of formula (XI) and having the specific structure:

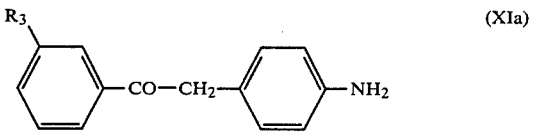

(XIa)

where $R_3$ = halogen or CN, are prepared by reduction by means of iron, in the presence of ammonium chloride, in an ethanol medium, of the nitrated compound of formula:

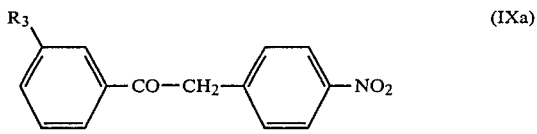

(IXa)

in which $R_3$ has the same meanings as in formula (XIa), the compounds of formula (IXa) being prepared in a way identical to that described for the preparation of the compounds of formula (IX), but from m-halogenobenzaldehyde or m-cyanobenzaldehyde instead of 4-benzyloxy n-butanal;

or by cyclisation by means of sodium methylate in a toluene solution, of the compound of formula:

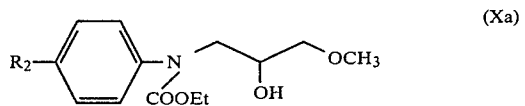

(Xa)

in which $R_2$ has the same meanings as in formula (X), obtained by action of ethyl chloroformate in solution in dichloroethane on the compound of formula:

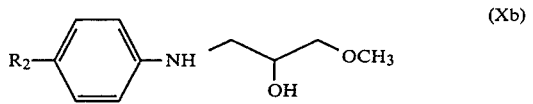

(Xb)

where $R_2$ has the same meanings as in formula (Xa), the compounds of formula (Xb) being themselves obtained by condensation of the compound of formula (XI) with 1-chloro 3-methoxy 2-propanol.

D. The compounds of formula (I) in which R designates the m-halogenophenetyl or m-cyanophenetyl chain are obtained by reduction, preferably by means of triethylsilane (SiEt$_3$H) in the presence of trifluoroacetic acid, of the formula (I) compound in which R designates the m-halogenobenzoylmethyl or m-cyanobenzoylmethyl group, the synthesis of these specific formula (I) compounds being carried out in accordance with the processes described in the preceding paragraph C.

E. The formula (I) compounds, in which R represents the (2-cyclohexyl) ethynyl, (2-m-halogenophenyl) ethynyl or (2-m-cyanophenyl) ethynyl chain, are obtained by condensation, preferably in an H.M.P.T. medium of the copper salts of (2-cyclohexyl) ethyne, (2-m-halogenophenyl) ethyne and (2-m-cyanophenyl) ethyne with 3-p-iodophenyl 5-methoxymethyl 2-oxazolidinone prepared by cyclisation by means of phosgene of 3-p-iodophenylamino 1-methoxy propanol according to a procedure identical to the one used for the preparation of the formula (V) compound.

The above-mentioned copper salts may be readily obtained by using the processes described in Angew. Chem. Int. Edit., 9, 464 (1970); J.C.S. (1967), 578 and J.C.S. (1969), 2173.

F. The formula (I) compounds in which R designates an m-halogenophenetyloxy or m-cyanophenetyloxy group are obtained by condensation, in a T.H.F. medium, in the presence of triphenylphosphine and ethyl azobisdicarboxylate, of m-halogeno- or m-cyanophenetylalcohol with 3-p-hydroxyphenyl 5-methoxymethyl 2-oxazolidinone prepared as described in Belgian Pat. No. 876 831.

G. The formula (I) compounds in which R designates an m-halogenophenoxymethyl or m-cyanophenoxymethyl group are obtained:

either by condensation, preferably in a T.H.F. medium and in the presence of triphenylphosphine and ethyl azobisdicarboxylate (EtOCO—N=N—COOEt), of m-halogenophenol or m-cyanophenol with 3-p-(hydroxymethyl) phenyl 5-methoxymethyl 2-oxazolidinone, this latter being obtained by reduction preferably by means of sodium borohydride, of 3-p-formylphenyl 5-methoxymethyl 2-oxazolidinone itself obtained by acid hydrolysis of the compound of formula:

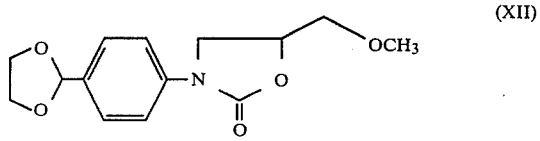
(XII)

obtained, for its part, by cyclisation by means of ethanolic potash or sodium methylate, of the compound of formula:

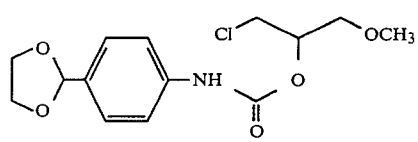
(X')

obtained according to the process already described for the synthesis of formula (X) compounds;

or by condensation, preferably in a DMF medium in the presence of sodium hydride, of 3-para-(hydroxymethyl) phenyl 5-methoxymethyl 2-oxazolidinone mesylate with m-halogeno- or m-cyanophenol.

The following examples are given to illustrate the invention.

EXAMPLE 1

3-para-(2-acetyl) ethoxyphenyl 5-methoxymethyl 2-oxazolidinone (I)

Code number: 238

A solution of 3.4 g of formula (II) compound and 5 ml of hydrochloric acid in 50 ml of acetone was stirred for two hours at ambient temperature, then 1 ml of ~2 N sulfuric acid was added and it was left stirring for a further 5 hours. It was neutralized with a solution of sodium bicarbonate, extracted with methylene chloride, dried on sodium sulfate, filtered, the filtrate was evaporated, the residue crystallized in alcohol, then re-crystallized in a mixture of alcohol and isopropylic ether. Thus, 1 g of the expected compound was isolated.

Yield: 34%
Melting point: 98° C.
Empirical formula: $C_{15}H_{19}NO_5$
Molecular weight: 293.31
Elementary analysis:

|  | C | H | N |
|---|---|---|---|
| Calculated (%) | 61.42 | 6.53 | 4.78 |

-continued

|  | C | H | N |
|---|---|---|---|
| Obtained (%) | 61.70 | 6.59 | 4.70 |

EXAMPLE 2

3-para-[2-(2-methyl 1,3-dioxanyl) ethoxy] phenyl 5-methoxymethyl 2-oxazolidinone (II)

To a solution of 5.6 g of 3-para-hydroxyphenyl 5-hydroxymethyl 2-oxazolidinone (III) in 100 ml of D.M.F. was added by small fractions 1.2 g of 50% sodium hydride. Then 9 g of 2-(2-bromo) ethyl 2-methyl 1,3-dioxolane in 20 ml of D.M.F. were added and the mixture was brought for three hours to 70°–80° C. Then it was poured into iced water, extracted with ethyl acetate, washed with water, dried on sodium sulfate, filtered, the filtrate was evaporated and the residue chromatographed on a silica column. By elution with methylene chloride-acetone mixtures [(98–2) then (95–5)], 5.6 g of the expected compound were obtained which was recrystallized in isopropylic ether.

Yield: 65%
Melting point: 56° C.
Empirical formula: $C_{17}H_{23}NO_6$
Molecular weight: 337.36
Elementary analysis:

|  | C | H | N |
|---|---|---|---|
| Calculated (%) | 60.52 | 6.87 | 4.15 |
| Obtained (%) | 60.31 | 7.03 | 4.04 |

EXAMPLE 3

5-benzyloxy 1-para-nitrophenyl 1-pentanone (IX)

To a solution of 105 g of α-phenylamino p-nitrobenzylester diphenylphosphorous acid in 1200 ml of T.H.F., cooled to −40° C., was added a solution of 12.8 g of potash in 128 ml of methanol, then a solution of 40.6 g of 4-benzyloxy n-butanal in 500 ml of THF within 30 minutes, and it was left for 2 hours at −40° C., then for 12 hours at room temperature. Then the solvents were evaporated, the residue taken up in water, extracted with ethyl acetate, the solvent was evaporated and the residue triturated in concentrated hydrochloric acid. It was diluted with water, extracted with ether, the solvent was evaporated and the residue crystallized in isopropylic ether. Thus, 23 g of the expected compound were obtained.

Yield: 38%
Melting point: 75° C.
Empirical formula: $C_{18}H_{19}NO_4$
Molecular weight: 313.34

By the same process, but from the corresponding reagents, the compounds of formula (IXa) were obtained.

EXAMPLE 4

5-benzyloxy 1-para-aminophenyl 1-pentanone (VIII)

A mixture of 23 g of formula (IX) compound obtained in the preceding example and 23 g of powdered iron in 200 ml of an aqueous solution of 10% ammonium chloride and 20 ml of ethanol was left under agitation for an hour at room temperature. Then it was extracted with methylene chloride, filtered, the filtrate was washed with water, dried on sodium sulfate, filtered, the filtrate was evaporated and the residue crystallized in a mixture of ethyl acetate and isopropylic ether. 18.6 g of the expected compound were obtained.

Melting point: 72° C.
Empirical formula: $C_{18}H_{21}NO_2$
Molecular weight: 283.36

By the same process, but from the (IXa) compounds, the formula (XIa) compounds were obtained.

EXAMPLE 5

5-benzyloxy 1-para-aminophenyl pentane (VII)

To a mixture of 16 g of formula (VIII) compound obtained in the preceding example and 21 g of triethylsilane were added 30.1 ml of trifluoroacetic acid and it was left under agitation for 20 hours at room temperature. Then, it was diluted with water, basified by means of concentrated NaOH, extracted with methylene chloride, washed with water, dried on sodium sulfate, the filtrate was evaporated and the residue chromatographed on a silica column [eluent: methylene chloride (99)-methanol (1) mixture]. Thus, 14 g of the expected compound were obtained in the form of an oil (Yield: 92%).

NMR spectrum, (CDCl₃) δppm=7.3,s, and 6.8, m (9 aromatic protons); 4.5, s, φ—C$\underline{H}$₂O; 3.4, m, (O—C$\underline{H}$₂— and N$\underline{H}$₂); 2.5, m, and 1.5, m,

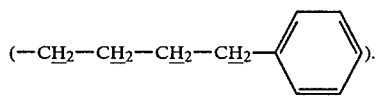

By the same process, but from the corresponding reagents, the formula (I) compounds having code numbers 271 and 272 appearing in table I were obtained.

EXAMPLE 6

1-para-(5-benzyloxy n-pentyl) phenylamino 3-methoxy 2-propanol (VI)

To a solution brought to reflux of 13.9 g of formula (VII) compound, obtained in the preceding example, in 80 ml of ethanol was added in the course of 4 hours a solution of 4.61 g of 3-methoxy 1,2-epoxy propane in 80 ml of ethanol. It was left a further 5 hours at reflux, then the solvent was evaporated and the residue chromatographed on a silica column [eluent: methylene chloride (98.9%) - methanol (1%) - ammonia (0.1%)]. Thus, 11 g of the expected compound were isolated in the form of an oil.

Yield: 61%

NMR spectrum (CDCl₃) δppm=7.3,s, and 6.7,m, (9 aromatic protons); 4.5,s, (φ—C$\underline{H}$₂O); 4,m,

3.6 to 2.8, m, (11 protons, N$\underline{H}$, OC$\underline{H}$₂, OC$\underline{H}$₃ and

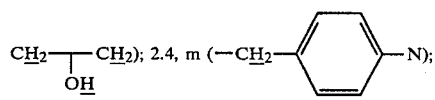

1.5, m, (—CH₂C$\underline{H}$₂—CH₂—).

EXAMPLE 7

3-para- (5-benzyloxy n-pentyl) phenyl 5-methoxymethyl 2-oxazolidinone (V)

To a solution of 10.3 g of formula (VI) compound obtained in the preceding example and 8.3 g of potassium carbonate in 150 ml of dichlorethane, were slowly added, while keeping the temperature at 20° C., 36 ml of a 10% phosgene solution in dichlorethane and it was left under agitation for 15 minutes, then brought to 50° C. for 5 hours. Then it was washed with a solution of sodium bicarbonate, with water, dried on sodium sulfate, the filtrate was evaporated and the residue chromatographed on a silica column [eluent: ethyl acetate (40%) - hexane (60%)]. Thus, 10.3 g of the expected compound were obtained in the form of an oil.

Yield: 89%

NMR spectrum (CDCl₃) δppm=7.3,m, (9 aromatic H); 4.6,m,

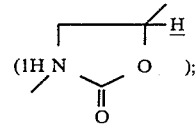

4.5, s, (φC$\underline{H}$₂O); 4.2 to 3.3, m, (9 H: O—C$\underline{H}$₂—,

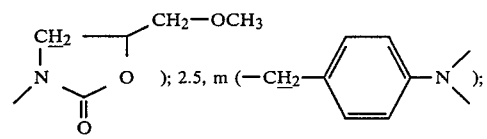

1.5, m, (—C$\underline{H}$₂CH₂C$\underline{H}$₂—);

EXAMPLE 8

3-para-(5-hydroxy 1-n-pentyl) phenyl 5-methoxymethyl 2-oxazolidinone (IV)

A suspension of 10 g of formula (V) compound obtained in the preceding example and 2 g of palladium on charcoal (at 5%) in 300 ml of 96° ethanol was hydrogenolysed at normal pressure and room temperature for 2 hours in an autoclave. Then it was filtered, the filtrate was evaporated and an oil was obtained which crystallizes.

Melting point: <50° C.
Empirical formula: $C_{16}H_{23}NO_3$
Molecular weight: 277.35

NMR spectrum (CDCl₃) δppm=7.3, m, (4 aromatic H)

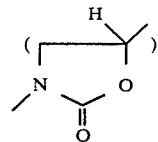

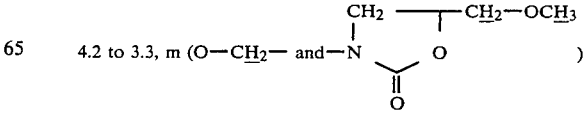

4.2 to 3.3, m (O—C$\underline{H}$₂— and—N 2.5, m, (HO and —CH₂— 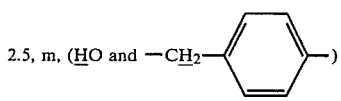)

1.5, m, (—CH₂—CH₂—CH₂—)

EXAMPLE 9

3-para-[(5-cyano 1-n-pentyl) phenyl] 5-methoxymethyl 2-oxazolidinone (I)

Code number: 289

To a solution cooled at 0° C. of 5.7 g of formula (IV) compound obtained in the preceding example and of 7 ml of triethylamine in 180 ml of methylene chloride, were slowly added 3.2 g of mesyl chloride. Then the obtained mixture is stirred during 1 hour at room temperature, washed with water, dried on sodium sulfate, filtered and evaporated. The residue (7.9 g) is dissolved in 60 ml of D.M.S.O. and then added to a solution of 1.4 g of potassium cyanide in 70 ml of D.M.S.O. The mixture is brought to 50°-60° C. during 7 hours, diluted with water, extracted with methylene chloride, washed with water, dried on sodium sulfate, filtered and the filtrate is evaporated, the residue being chromatographed on a silica column [eluents: hexane-ethyl acetate (60-40) and (50—50)]. Thus, 5.6 g of the expected compound (oil) were isolated.

Yield: 96%

NMR Spectrum (CDCl₃) δppm=7.3,m,:4 aromatic H

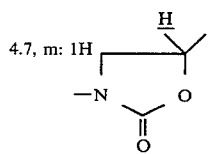
4.7, m: 1H

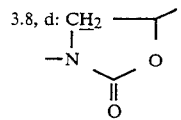
3.8, d: CH₂

3.5, d, (J=3 Hz):—CH₂O—; 3.4, s: O—CH₃; 2.4,m:CN—CH₂— and

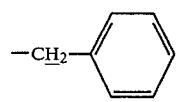

1.5, m: (—CH₂—CH₂—CH₂—)

Empirical formula: C₁₇H₂₂N₂O₃
Molecular weight: 302.36
Elementary analysis:

|  | C | H | N |
|---|---|---|---|
| Calculated (%) | 67.53 | 7.33 | 9.27 |
| Obtained (%) | 67.23 | 7.51 | 9.18 |

EXAMPLE 10

3-para-(4-chlorophenyl) phenyl 5-methoxymethyl 2-oxazolidinone (I)

Code number: 269

To a solution of 0.9 g of formula (X) compound [R₂=para-chlorophenyl] in 70 ml of ethanol was added a solution of 0.17 g of potash in 1 ml of ethanol and the whole was left under agitation for 45 minutes. Then it was poured in iced water, extracted with ethyl acetate, washed with water, with a 1 N hydrochloric acid solution, with water, dried on sodium sulfate, filtered and the residue was evaporated and re-crystallized in isopropylic acid.

Yield: 69%
Melting point: 140° C.
Empirical formula: C₁₇H₁₆ClNO₃
Molecular weight: 317.76
Elementary analysis:

|  | C | H | N |
|---|---|---|---|
| Calculated (%) | 64.25 | 5.08 | 4.41 |
| Obtained (%) | 64.00 | 4.90 | 4.36 |

By the same process, but from the corresponding reagents, the formula (I) compounds having code numbers 284, 270 and 274 appearing in table I below were obtained.

EXAMPLE 11

3-para-[1-(2-meta-chlorophenyl ethynyl)] phenyl 5-methoxymethyl 2-oxazolidinone (I)

Code number: 277

A mixture of 4.8 g of copper salt of meta-chlorophenylethynyl and 6.7 g of 3-p-iodophenyl 5-methoxymethyl 2-oxazolidinone in 100 ml of H.M.P.T. was brought to 220°-230° C., in a nitrogen stream, for 1½ hour. Then it was poured into water, extracted with ethyl acetate, washed with water, then with a potassium iodide solution, then with water, dried on sodium sulfate, filtered, the filtrate was evaporated and the residue crystallized in methanol.

Yield: 27%
Melting point: 120° C.
Empirical formula: C₁₉H₁₆ClNO₃
Molecular weight: 341.78
Elementary analysis:

|  | C | H | N |
|---|---|---|---|
| Calculated (%) | 66.76 | 4.72 | 4.10 |
| Obtained (%) | 66.20 | 4.64 | 4.04 |

By the same process, but from the corresponding reagents, the formula (I) compounds appearing in table I below under code numbers 281 and 282 were obtained.

EXAMPLE 12

3-para-(meta-cyanophenetyloxy) phenyl 5-methoxymethyl 2-oxazolidinone (I)

Code number: 267

To a solution, cooled to 0° C., of 2.2 .g of 3-para-hydroxyphenyl 5-methoxymethyl 2-oxazolidinone, 3.4 g of triphenylphosphine and 1.5 g of metacyanophenetylalcohol in 50 ml of T.H.F. were added, under a stream of nitrogen, 2.1 ml of ethyl azobisdicarboxylate. Then it was left under agitation for 14 hours at 20° C., the solvent was evaporated and the residue chromatographed on a silica column [eluent: heptane-ethylacetate (50—50)]. Thus the expected compound was isolated which was re-crystallized in methanol.
Yield: 32%
Melting point: 60° C.
Empirical formula: $C_{20}H_{20}N_2O_4$
Molecular weight: 352.38
Elementary analysis:

|  | C | H | N |
|---|---|---|---|
| Calculated (%) | 68.17 | 5.72 | 7.95 |
| Obtained (%) | 68.06 | 5.76 | 8.00 |

By the same process, but from the corresponding reagents, the formula (I) compounds appearing in table I below under code numbers 273, 275 and 264 were obtained.

EXAMPLE 13

3-para-(hydroxymethyl) phenyl 5-methoxymethyl 2-oxazolidinone

To a solution of 37.4 g of 3-para-formylphenyl 5-methoxymethyl 2-oxazolidinone in 200 ml of ethanol were slowly added 12 g of sodium borohydride, then it was brought to reflux for 2 hours, the solvent was evaporated, the residue was taken up in water, extracted with ethyl acetate, washed with water, dried on sodium sulfate, filtered and the solvent evaporated. The expected product was obtained with a yield of 54%.
Melting point: 70° C.
Empirical formula: $C_{15}H_{15}NO_4$ Elementary analysis

|  | C | H | N |
|---|---|---|---|
| Calculated (%) | 60.75 | 6.37 | 5.90 |
| Obtained (%) | 60.71 | 6.31 | 6.12 |

EXAMPLE 14

3-para-(metacyano) phenoxymethylphenyl 5-methoxymethyl 2-oxazolidinone (I)

Code number: 275

To a suspension of 3.5 g of 3-cyanophenol in 50 ml of D.M.F. were added 1.4 g of 50% sodium hydride then 6 g of 3-para-(hydroxymethyl)phenyl 5-methoxymethyl 2-oxazolidinone mesylate prepared by action of mesyl chloride in the presence of triethylamine. The mixture was brought up to 100° C. for 3 hours. Then it was poured into water, extracted with ethyl acetate, washed with water, dried on sodium sulfate, filtered, the filtrate was evaporated and the residue crystallized in absolute alcohol. The product expected was obtained with a yield of 59%.
Melting point: 86° C.
Empirical formula: $C_{19}H_{18}N_2O_4$
Molecular weight: 338.35
Elementary analysis:

|  | C | H | N |
|---|---|---|---|
| Calculated (%) | 67.44 | 5.36 | 8.28 |
| Obtained (%) | 67.45 | 5.23 | 8.29 |

By the same process, but from the corresponding reagents, the formula (I) compound appearing in table I below under code number 273 was obtained.

TABLE I

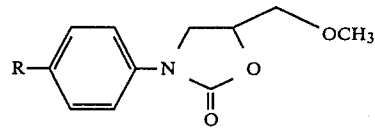

(I)

| Code Number | R | Empirical formula | Molecular weight | Melting point (°C.) | Yield (%) | | ELEMENTARY ANALYSIS | | |
|---|---|---|---|---|---|---|---|---|---|
|  |  |  |  |  |  | % | C | H | N |
| 238 | $CH_3-CO-(CH_2)_2-O-$ | $C_{15}H_{19}NO_5$ | 293.31 | 98 | 34 | Cal. | 61.42 | 6.53 | 4.78 |
|  |  |  |  |  |  | Obt. | 61.70 | 6.59 | 4.70 |
| 289 | $CN-(CH_2)_5-$ | $C_{17}H_{22}N_2O_3$ | 302.36 |  | 96 | Cal. | 67.53 | 7.33 | 9.27 |
|  |  |  |  |  |  | Obt. | 67.23 | 7.51 | 9.18 |
| 269 | Cl—⟨phenyl⟩— | $C_{17}H_{16}ClNO_3$ | 317.76 | 140 | 69 | Cal. | 64.25 | 5.08 | 4.41 |
|  |  |  |  |  |  | Obt. | 64.00 | 4.90 | 4.36 |
| 284 | CN—⟨phenyl⟩— | $C_{18}H_{16}N_2O_3$ | 308.32 | 70 | 50 | Cal. | 70.11 | 5.23 | 9.09 |
|  |  |  |  |  |  | Obt. | 69.90 | 5.12 | 8.92 |
| 281 | ⟨cyclohexyl⟩—C≡C— | $C_{19}H_{23}NO_3$ | 312.38 | 86 | 18 | Cal. | 72.82 | 7.40 | 4.47 |
|  |  |  |  |  |  | Obt. | 72.54 | 7.73 | 4.56 |
| 271 | Cl—⟨phenyl⟩—$CH_2-CH_2-$ | $C_{19}H_{20}ClNO_3$ | 345.81 | 62 | 37 | Cal. | 65.99 | 5.83 | 4.05 |
|  |  |  |  |  |  | Obt. | 66.14 | 5.85 | 4.09 |

TABLE I-continued

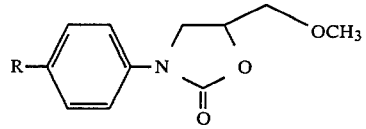
(I)

| Code Number | R | Empirical formula | Molecular weight | Melting point (°C.) | Yield (%) | ELEMENTARY ANALYSIS % | C | H | N |
|---|---|---|---|---|---|---|---|---|---|
| 272 | CN-C₆H₄-CH₂-CH₂- | $C_{20}H_{20}N_2O_3$ | 336.38 | 102 | 40 | Cal. Obt. | 71.41 71.51 | 5.99 5.90 | 8.33 8.37 |
| 270 | CN-C₆H₄-CO-CH₂- | $C_{20}H_{18}N_2O_4$ | 350.36 | 92 | 60 | Cal. Obt. | 68.56 68.56 | 5.18 5.18 | 8.00 8.00 |
| 274 | Cl-C₆H₄-CO-CH₂- | $C_{19}H_{18}ClNO_4$ | 359.80 | 50 | 82 | Cal. Obt. | 63.42 63.30 | 5.04 4.96 | 3.89 3.95 |
| 273 | Cl-C₆H₄-O-CH₂- | $C_{18}H_{18}ClNO_4$ | 347.79 | 82 | 22 | Cal. Obt. | 62.16 62.22 | 5.22 5.26 | 4.03 4.01 |
| 275 | CN-C₆H₄-O-CH₂- | $C_{19}H_{18}N_2O_4$ | 338.35 | 86 | 59 | Cal. Obt. | 67.44 67.45 | 5.36 5.23 | 8.28 8.29 |
| 277 | Cl-C₆H₄-C≡C- | $C_{19}H_{16}ClNO_3$ | 341.78 | 120 | 27 | Cal. Obt. | 66.76 66.20 | 4.72 4.64 | 4.10 4.04 |
| 282 | CN-C₆H₄-C≡C- | $C_{20}H_{16}N_2O_3$ | 332.34 | 98 | 25 | Cal. Obt. | 72.27 72.34 | 4.85 4.72 | 8.43 8.53 |
| 264 | Cl-C₆H₄-CH₂-CH₂-O- | $C_{19}H_{20}ClNO_4$ | 361.81 | 50 | 19 | Cal. Obt. | 63.07 63.37 | 5.57 5.70 | 3.87 3.63 |
| 267 | CN-C₆H₄-CH₂-CH₂-O- | $C_{20}H_{20}N_2O_4$ | 352.38 | 60 | 32 | Cal. Obt. | 68.17 68.06 | 5.72 5.76 | 7.95 8.00 |

The compounds of formula (I) were tested on laboratory animals and showed activities in the psychotropic field as potential anti-depressants.

These activities were brought out in the following tests:

Test A: potentiation in mice of generalized trembling caused by an intraperitoneal injection (200 mg/kg) of dl-5-hydroxytryptophane, according to the procedure described by Gouret C. and Raynaud G. in J. Pharmacol. (Paris) (1974), 5, 231.

Test B: antagonism with respect to ptosis observed an hour after an intravenous injection (2 mg/kg) of reserpine in mice according to the procedure described by Gouret C. and Thomas J. in J. Pharmacol. (Paris), (1973), 4, 401.

The results of these tests, as well as those of a reference substance, TOLOXATONE, are given in table II below.

TABLE II

| Tested compound | Test A ED 50 (mg/kg/p.o.) | Test B ED 50 (mg/kg/p.o.) | Toxicity (mice) LD 50 (mg/kg/p.o.) |
|---|---|---|---|
| 238 | 1.9 | 1.1 | >1000 |
| 264 | 2.8 | 3 | " |
| 267 | 1.8 | 1.3 | " |
| 269 | 1.7 | 1.2 | " |
| 270 | 0.2 | 0.2 | " |
| 271 | 4.1 | 3.8 | " |
| 272 | 0.5 | 0.4 | " |
| 273 | 5.9 | 3.4 | " |
| 274 | 1.2 | 0.9 | " |
| 275 | 0.6 | 0.3 | " |
| 277 | 1.2 | 1.7 | " |
| 281 | 1.3 | 0.6 | " |
| 282 | 0.3 | 0.3 | " |
| 284 | 1.2 | 1.3 | " |
| 289 | 0.15 | 0.2 | " |

TABLE II-continued

| Tested compound | Test A ED 50 (mg/kg/p.o.) | Test B ED 50 (mg/kg/p.o.) | Toxicity (mice) LD 50 (mg/kg/p.o.) |
| --- | --- | --- | --- |
| TOLOXATONE | 60 | 50 | — |

It can be seen from the results collected in Table II that the compounds of the invention are far more active than Toloxatone, a well-known reference compound.

The compounds of the present application form then drugs which are particularly suitable in the treatment of endogenous and exogenous depressive conditions.

The present invention also relates to pharmaceutic compositions comprising at least one compound of formula (I) if necessary in association with a pharmaceutically acceptable carrier. These compositions may be administered:

either orally in the form of tablets, pills or capsules, at a dosage of 50 to 500 mg/day on average of active constituent, or in the form of an injectable aqueous solution, at a dosage of 5 to 50 mg/day of active constituent; the solvent used is formed of binary or ternary mixtures containing for example water, polypropylene glycol, polyethyleneglycol 300 or 400, or any other physiological solvent, the relative proportions of the different constituents being adjusted depending on the dose administered.

What is claimed is:

1. A compound having the formula

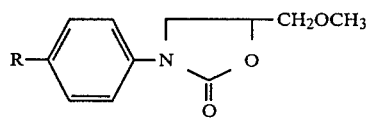

in which R is selected from the group consisting of $CH_3-CO-(CH_2)_2-O-$, $CN-(CH_2)_5-$,

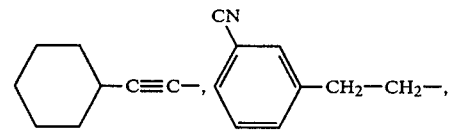

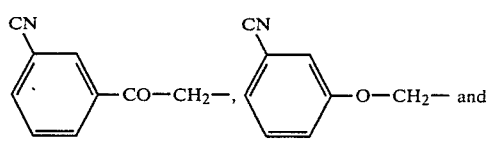

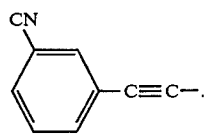

2. A compound as claimed in claim 1 in which R is $CH_3-CO-(CH_2)_2-O-$.

3. A compound as claimed in claim 1 in which R is $CN-(CH_2)_5-$.

4. A compound as claimed in claim 1 in which R is

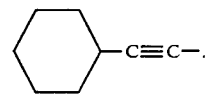

5. A compound as claimed in claim 1 in which R is

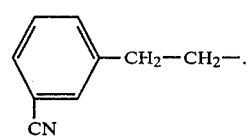

6. A compound as claimed in claim 1 in which R is

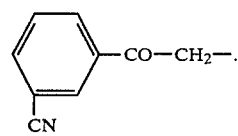

7. A compound as claimed in claim 1 in which R is

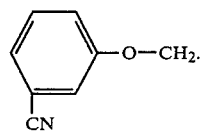

8. A compound as claimed in claim 1 in which R is

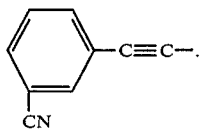

9. A pharmaceutical composition for treating depression comprising a therapeutically effective amount of a compound as claimed in claim 1, in combination with a pharmaceutically effective carrier.

* * * * *